US 9,801,587 B2

(12) United States Patent
MacDonald et al.

(10) Patent No.: US 9,801,587 B2
(45) Date of Patent: Oct. 31, 2017

(54) HEART RATE MONITOR WITH TIME VARYING LINEAR FILTERING

(71) Applicant: Garmin Switzerland GmbH, Schaffhausen (CH)

(72) Inventors: Paul R. MacDonald, Calgary (CA); Christopher J. Kulach, Calgary (CA)

(73) Assignee: Garmin Switzerland GmbH (CH)

( * ) Notice: Subject to any disclaimer, the term of this patent is extended or adjusted under 35 U.S.C. 154(b) by 0 days.

(21) Appl. No.: 15/296,956

(22) Filed: Oct. 18, 2016

(65) Prior Publication Data

US 2017/0105682 A1    Apr. 20, 2017

Related U.S. Application Data

(60) Provisional application No. 62/243,447, filed on Oct. 19, 2015.

(51) Int. Cl.
*A61B 5/00* (2006.01)
*A61B 5/083* (2006.01)
(Continued)

(52) U.S. Cl.
CPC .......... *A61B 5/721* (2013.01); *A61B 5/02405* (2013.01); *A61B 5/02427* (2013.01); *A61B 5/02438* (2013.01); *A61B 5/0833* (2013.01); *A61B 5/165* (2013.01); *A61B 5/486* (2013.01); *A61B 5/4815* (2013.01); *A61B 5/681* (2013.01); *A61B 5/725* (2013.01); *A61B 5/7278* (2013.01); *A61B 2562/0219* (2013.01)

(58) Field of Classification Search
None
See application file for complete search history.

(56) References Cited

U.S. PATENT DOCUMENTS 6,178,343 B1    1/2001    Bindszus ...................... 600/323
6,702,752 B2    3/2004    Dekker ......................... 600/484
(Continued)

FOREIGN PATENT DOCUMENTS

WO    WO2006/067690 A2    6/2006
WO    WO2011/051888 A2    5/2011
(Continued)

OTHER PUBLICATIONS

U.S. Appl. No. 15/296,938, filed Oct. 18, 2016.

*Primary Examiner* — Brian T Gedeon
(74) *Attorney, Agent, or Firm* — Samuel M. Korte; Max M. Ali (57) ABSTRACT

A system, method, and device for monitoring a cardiac signal of a user includes an emitter (LED) for transmitting light toward skin of the user, a receiver (photodiode) for receiving a reflection of the transmitted light and generating a light intensity signal, and a processor configured to generate a photoplethysmogram (PPG) signal based on the light intensity signal. The PPG signal includes a cardiac component, a motion component and a respiratory component. An inertial sensor provides a motion signal to the processor based on sensed movement of the device and one or more time-variant filters are configured by the processor to filter the PPG signal to isolate the cardiac component of the PPG signal based on determined filter coefficients.

29 Claims, 7 Drawing Sheets

(51) Int. Cl.
*A61B 5/16* (2006.01)
*A61B 5/027* (2006.01)
*A61B 5/024* (2006.01)

(56) References Cited

U.S. PATENT DOCUMENTS

| | | | |
|---|---|---|---|
| 6,997,879 B1 | 2/2006 | Turcott | 600/507 |
| 7,035,679 B2 | 4/2006 | Addison | 600/323 |
| 7,336,982 B2 | 2/2008 | Yoo | 600/323 |
| 7,470,234 B1 | 12/2008 | Elhag | 600/485 |
| 7,625,344 B1 | 12/2009 | Brady | 600/485 |
| 7,729,748 B2 | 6/2010 | Florian | 600/476 |
| 7,867,142 B2 | 1/2011 | Kim | 482/8 |
| 8,109,874 B2 | 2/2012 | Kong | 600/300 |
| 8,251,903 B2 | 8/2012 | LeBoeuf et al. | 600/309 |
| 8,260,405 B2 | 9/2012 | Aarts | 600/509 |
| 8,460,199 B2 | 6/2013 | Rulkov | 600/503 |
| 8,463,347 B2 | 6/2013 | Watson | 600/324 |
| 8,509,882 B2 | 8/2013 | Albert | 600/509 |
| 8,512,242 B2 | 8/2013 | LeBoeuf et al. | 600/309 |
| 8,554,297 B2 | 10/2013 | Moon | 600/310 |
| 8,591,411 B2 | 11/2013 | Banet | 600/300 |
| 8,647,270 B2 | 2/2014 | LeBoeuf et al. | 600/301 |
| 8,652,040 B2 | 2/2014 | LeBoeuf et al. | 600/301 |
| 8,670,123 B2 | 3/2014 | Schleipen | 356/445 |
| 8,700,111 B2 | 4/2014 | LeBoeuf et al. | 600/310 |
| 8,788,002 B2 | 7/2014 | LeBoeuf et al. | 600/310 |
| 8,827,906 B2 | 9/2014 | Yuen | 600/301 |
| 8,886,269 B2 | 11/2014 | LeBoeuf et al. | 600/310 |
| 8,888,701 B2 * | 11/2014 | LeBoeuf | G06F 19/3406 600/301 |
| 8,923,941 B2 | 12/2014 | LeBoeuf et al. | 600/310 |
| 8,929,965 B2 | 1/2015 | LeBoeuf et al. | 600/310 |
| 8,929,966 B2 | 1/2015 | LeBoeuf et al. | 600/310 |
| 8,934,952 B2 | 1/2015 | LeBoeuf et al. | 600/310 |
| 8,942,776 B2 | 1/2015 | LeBoeuf et al. | 600/310 |
| 8,945,017 B2 | 2/2015 | Venkatraman | 600/500 |
| 8,954,135 B2 | 2/2015 | Yuen | 600/476 |
| 8,989,830 B2 | 3/2015 | LeBoeuf et al. | 600/310 |
| 8,998,815 B2 | 4/2015 | Venkatraman | 600/300 |
| 9,005,129 B2 | 4/2015 | Venkatraman | 600/300 |
| 9,039,614 B2 | 5/2015 | Yuen | |
| 9,044,171 B2 | 6/2015 | Venkatraman | 342/357.74 |
| 9,044,180 B2 | 6/2015 | LeBoeuf et al. | 600/310 |
| 9,131,312 B2 | 9/2015 | LeBoeuf et al. | |
| 9,289,135 B2 | 3/2016 | LeBoeuf et al. | 600/310 |
| 9,289,175 B2 | 3/2016 | LeBoeuf et al. | 600/310 |
| 9,301,696 B2 | 4/2016 | LeBoeuf et al. | 600/310 |
| 9,307,917 B2 | 4/2016 | Hong et al. | |
| 9,314,167 B2 | 4/2016 | LeBoeuf et al. | 600/310 |
| 9,538,921 B2 | 1/2017 | LeBoeuf et al. | |
| 2005/0143665 A1 | 6/2005 | Huiku | 600/500 |
| 2009/0048526 A1 | 2/2009 | Aarts | 600/508 |
| 2009/0105556 A1 | 4/2009 | Fricke | 600/301 |
| 2010/0113948 A1 | 5/2010 | Yang | 600/500 |
| 2011/0082355 A1 | 4/2011 | Eisen | 600/324 |
| 2012/0197137 A1 | 8/2012 | Jeanne | 600/479 |
| 2013/0231926 A1 | 9/2013 | Gigi | 704/207 |
| 2014/0213858 A1 | 7/2014 | Presura | 600/301 |
| 2014/0276099 A1 | 9/2014 | Kirenko | 600/476 |
| 2014/0288436 A1 | 9/2014 | Venkatraman | 600/479 |
| 2014/0316305 A1 | 10/2014 | Venkatraman | 600/595 |
| 2015/0173628 A1 | 6/2015 | Yuen | |
| 2015/0196256 A1 | 7/2015 | Venkatraman | |
| 2016/0051158 A1 * | 2/2016 | Silva | A61B 5/02416 600/479 |
| 2016/0317096 A1 * | 11/2016 | Adams | A61B 5/721 |
| 2016/0317097 A1 * | 11/2016 | Adams | A61B 5/721 |

FOREIGN PATENT DOCUMENTS

| | | |
|---|---|---|
| WO | WO2013/042070 A1 | 3/2013 |
| WO | WO2013/124750 A1 | 8/2013 |
| WO | WO2013/190423 A1 | 12/2013 |

* cited by examiner

HEART RATE MONITOR WITH TIME VARYING LINEAR FILTERING

CROSS-REFERENCE TO RELATED APPLICATIONS

The present patent application claims priority benefit under 35 U.S.C. §119(e), with regard to all common subject matter, of U.S. Provisional Application Ser. No. 62/243,447, filed Oct. 19, 2015, titled "PPG SIGNAL ANALYSIS," which is hereby incorporated by reference in its entirety. This application is related to simultaneously filed U.S. patent application Ser. No. 15/296,938, entitled "SYSTEM AND METHOD FOR GENERATING A PPG SIGNAL" the entire contents of which is expressly incorporated herein.

BACKGROUND

A user's heart rate is a physiological characteristic that may be used to determine and track one or more performance characteristics of the user. A photoplethysmogram (PPG) signal provides information that can be used to determine physiological metrics of an individual, such as a heartbeat signal and other cardiac information. Devices that generate a PPG signal using optical techniques typically include an emitter configured to output light toward skin of the user and a receiver, which may include a photodiode and electrical circuitry, configured to generate a light intensity signal based on a light reflections received from the photodiode and using the electrical circuitry to generate a PPG signal based on the light intensity signal. The PPG signal includes a cardiac component, a motion component and a respiratory component. The signal-to-noise ratio (SNR) for the desired cardiac component of a PPG signal is sensitive to movements of the user and/or a device configured to generate the PPG signal that is worn by the user. Even slight movements of the user or the device may rapidly degrade the SNR for the cardiac component of the PPG signal. Because the PPG signal is sensitive to such noise, the individual is typically still or motionless when physiological metrics are monitored.

Figure 1:
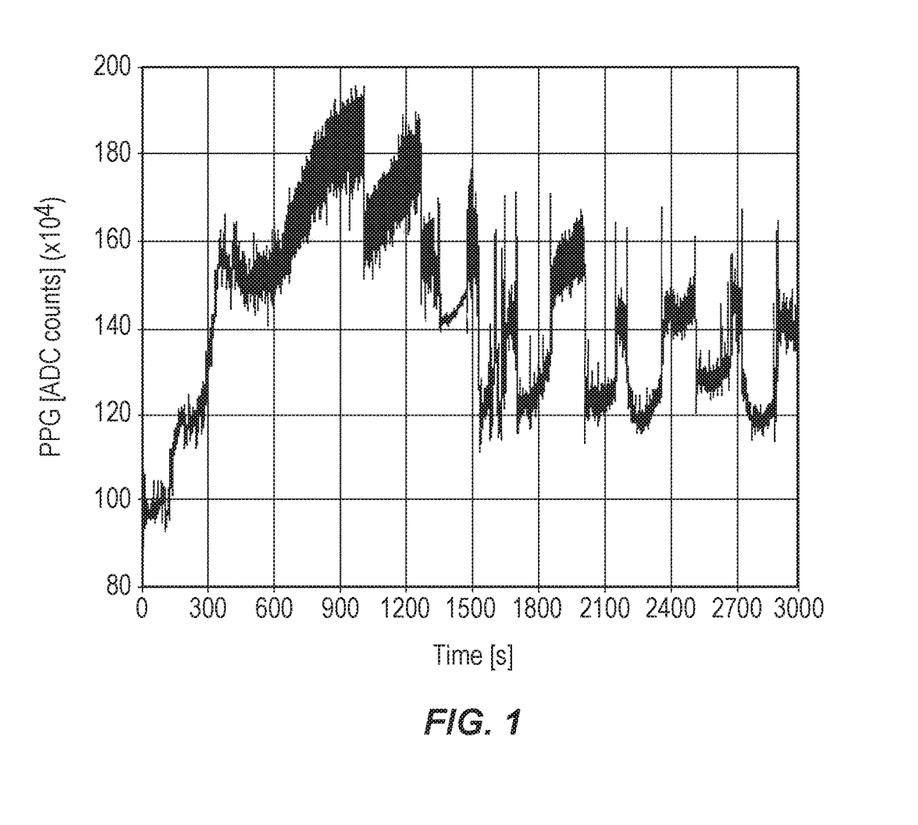
FIG. 1 is a graph of a PPG signal generated by a receiver while an individual is performing multiple types of physical movement, for example, walking, running and jogging.
Figure 2:
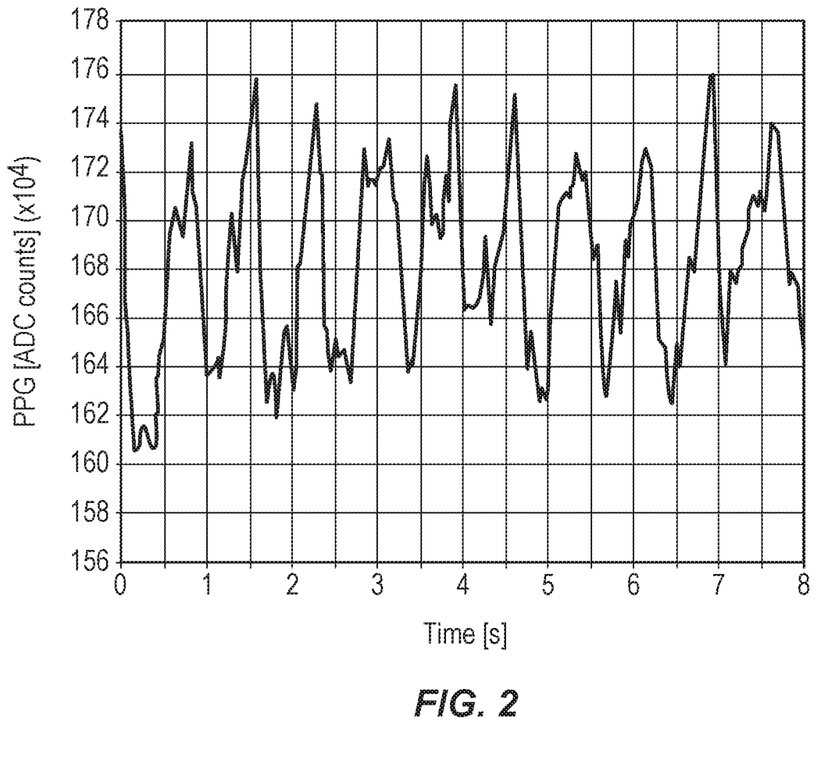
FIG. 2 is a graph of a PPG signal generated by a receiver while an individual is performing one type of physical movement, for example, jogging.
Figure 3:
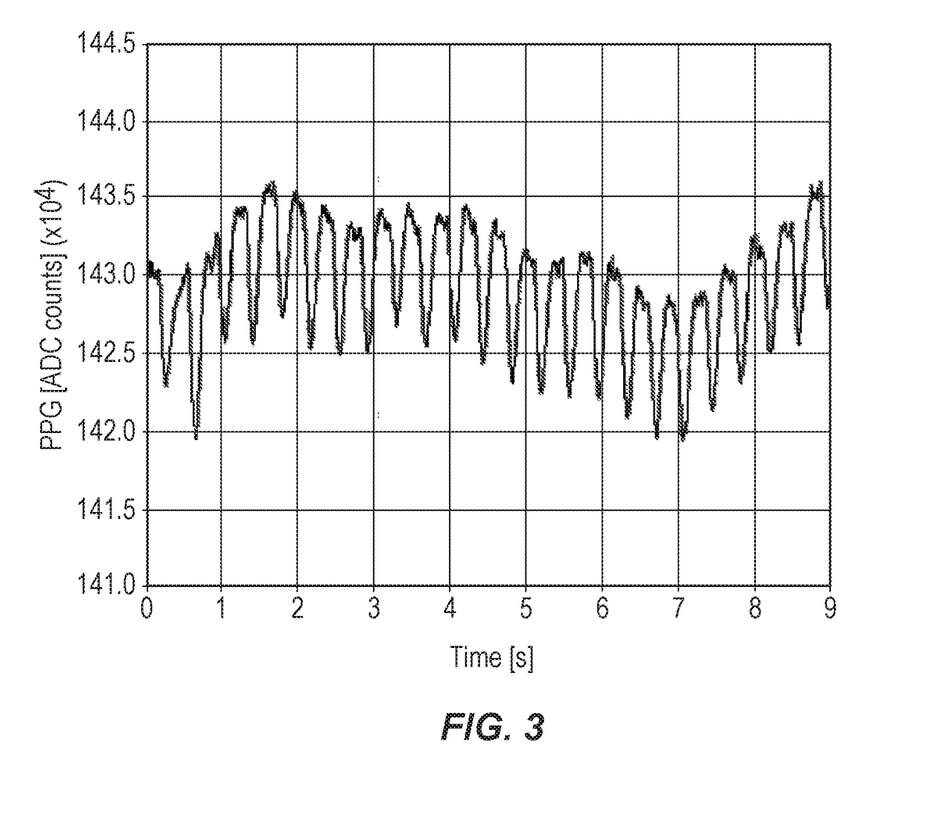
FIG. 3 is a graph of a PPG signal generated by a receiver while an individual is engaged in a sedentary activity, such as watching a movie.

The exemplary PPG signals illustrated in FIGS. 1 to 3 include artifacts from other interfering components generally attributed to a source of interference, such as movement of the device. For example, FIG. 1 depicts a PPG signal generated by a receiver based on received intensities of received light reflections from an individual engaged in walking (period from 0 to 150 seconds), running (period from 150 seconds to 1500 seconds) and jogging (period from 1500 seconds to 3000 seconds). The PPG signal of FIG. 1 depicts a dominant motion component associated with a cadence of the user in each activity type. Similarly, FIG. 2 depicts a PPG signal generated by a receiver based on received intensities of received light reflections from an individual engaged in a few strides of jogging over a duration of eight seconds. The PPG signal of FIG. 2 depicts a dominant motion component associated with a cadence of the user while jogging. FIG. 3 depicts a graph of a slightly drifting or undulating PPG signal, which includes a PPG signal generated by a receiver based on received intensities of received light reflections from an individual engaged in sedentary or comparatively idle activity over a period of approximately nine seconds. As can be readily observed from the PPG signals of FIGS. 1-3, the PPG signal of FIG. 3 is more stable (i.e., contains fewer motion components resulting from physical activity) than the PPG signals of FIGS. 2 and 3, which depict PPG signals associated with users engaged in more strenuous activity and thus relatively more motion components resulting from the user movement.

Unlike a medical environment in which a user may be sedentary (i.e., a patient receiving medical care receives attention while resting in a bed), typical daily activities, which may include moving, walking, running, swimming, driving, etc., may introduce interference effects on the PPG signal during such activities. It is desirable to minimize such interference effects to better determine the desired physiological aspect of the individual.

SUMMARY

In one aspect of the invention, a fitness monitor attached to a user for monitoring a cardiac signal of the user includes an emitter, a receiver, an inertial sensor, a time-variant filter and a memory. The emitter, which may comprise one or more LEDs, may be configured to transmit light toward skin of the user. The receiver, which may comprise one or more photodiodes and a photometric front end, may be configured to receive a reflection of the transmitted light and provide a photoplethysmogram (PPG) signal based on the received reflection of the transmitted light. The time-variant filter may receive the PPG signal, which includes a cardiac component and a motion component, and filter, in the time domain, an identified motion component from the PPG signal to facilitate determination of the cardiac component. The inertial sensor, such as an accelerometer or a gyroscope, may be configured to provide a motion signal based on sensed movement of the fitness monitor. The fitness monitor may further include a processor coupled to the emitter, the receiver, the inertial sensor and the time-variant filter, wherein the processor is configured to determine one or more frequencies associated with the motion signal, transform the PPG signal to the frequency domain, identify, in the frequency domain, the cardiac component in the PPG signal based on the determined one or more frequencies of the motion signal and the transformed PPG signal, determine filter coefficients based on the identified cardiac component in the PPG signal and configure the time-variant filter with the determined filter coefficients, and filter, in the time domain via the time-variant filter, the identified motion component from the PPG signal to facilitate determination of the cardiac component.

Another aspect of the invention is directed to a fitness monitor for monitoring a cardiac signal of a user. The fitness monitor may include an emitter configured to transmit light toward skin of the user, a receiver configured to receive a reflection of the transmitted light and provide a PPG signal based on the received reflection of the transmitted light, the PPG signal including a cardiac component and a motion component, an inertial sensor configured to provide a motion signal based on sensed movement of the fitness monitor, and a time-variant filter receiving the PPG signal. The fitness monitor may further include a processor coupled to the emitter, the receiver, the inertial sensor and the time-variant filter, wherein the processor is configured to determine one or more frequencies associated with the motion signal and the PPG signal provided during a first period, identify the motion component in the PPG signal for the first time period based on the determined one or more frequencies of the motion signal and the PPG signal, and filter, via the time-variant filter, the identified motion component for the first time period from the PPG signal provided during a second time period to facilitate determination of the cardiac component of the PPG signal for the second time period.

In a further aspect of the invention, a fitness monitor for monitoring a cardiac signal of a user includes an emitter configured to transmit light toward skin of the user, a receiver configured to receive a reflection of the transmitted light and provide a PPG signal based on the received reflection of the transmitted light, the PPG signal including a cardiac component and a motion component, an inertial sensor configured to provide a motion signal based on sensed movement of the fitness monitor, and a time-variant filter receiving the PPG signal. The fitness monitor may further include a processor coupled to the emitter, the receiver, the inertial sensor and the time-variant filter, wherein the processor is configured to determine one or more frequencies associated with the motion signal and the PPG signal provided during a first period, identify the cardiac component in the PPG signal for the first time period based on the determined one or more frequencies of the motion signal and the PPG signal, and filter, via the time-variant filter, the PPG signal provided for a second time to isolate the cardiac component of the PPG signal for the second time period based on the identified cardiac component for the first time period.

Many of the inventive principles and much of the inventive functionality may be implemented with or in software programs or instructions and integrated circuits (ICs) such as application specific ICs. It is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation. Therefore, in the interest of brevity and minimization of any risk of obscuring the principles and concepts in accordance to the present invention, further discussion of such software and ICs, if any, is limited to the essentials with respect to the principles and concepts of the described embodiments.

DETAILED DESCRIPTION

Aspects of the present invention extend the use of PPG signals for measurement of physiological metrics to the full range of human activities (e.g., stationary, sedentary, mobile, fitness, athletic training, etc.). In embodiments, techniques described herein may be implemented by a processor to identify and isolate a desired cardiac component within a PPG signal that has been generated based on sensory readings of an individual user engaged in various user activities, including activities with aggressive cyclical and irregular motion patterns. In embodiments, determination of the cardiac component may be desired and other components, such as movement and respiratory components, may be undesired. It is to be understood that the processor may desire to isolate the respiratory component in embodiments of the present invention. For example, configuration of the time-variant filters to isolate the respiratory component may be desired and other components, such as the cardiac and movement components, may be removed from the PPG signal.

A user's heartbeat and respiratory patterns are cyclical when observed of a short period of time (e.g., 5 seconds) and may vary when observed over an extended period of time. For instance, the user's heartbeat or breathing may become irregular when observed of an extended period of time (e.g., 5 minutes). Motion patterns and artifacts associated with a user may be cyclical, irregular or any combination thereof. The desired cardiac component of the PPG signal may include, but is not limited to, a heartbeat signal. A heart-rate may be determined for the user based on the heartbeat signal over a period of time. The PPG signal may also be analyzed by a processor to identify or determine other physiological parameters, such as a variability of the heartbeat signal, and present determined parameters to the user on a display.

Figure 4:
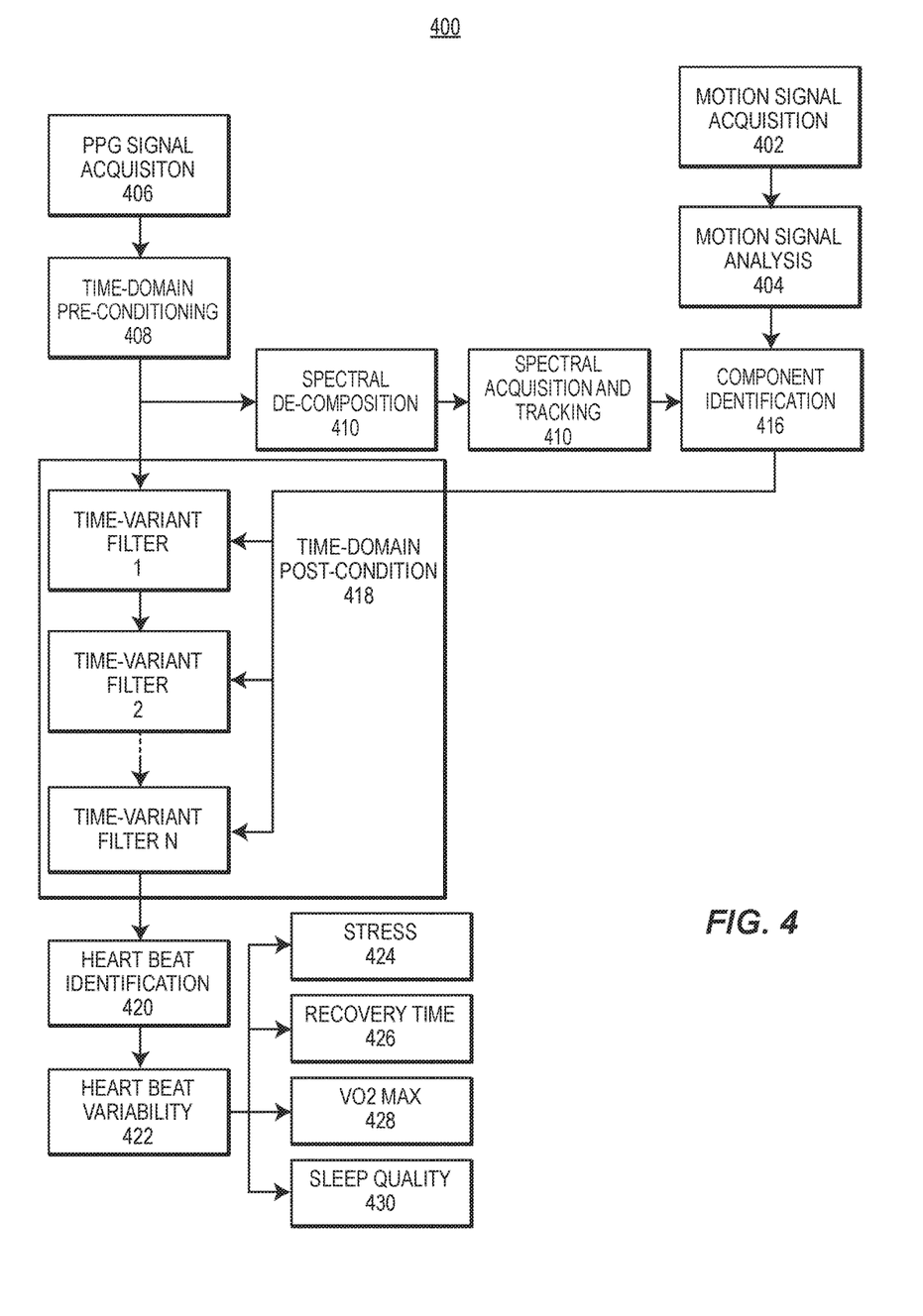
FIG. 4 depicts an exemplary process for operating a fitness monitor for monitoring a physiological characteristic of a user as described herein.

FIG. 4 depicts a block diagram of an exemplary process 400 for acquiring a PPG signal and using the PPG signal to isolate a cardiac component of the PPG signal, which is associated with a heartbeat of an individual user. The steps shown and described may be omitted, reordered, or otherwise changed in various configurations or embodiments; and additional steps may be added.

At block 402, one or more motion signals (e.g., linear acceleration, angular acceleration, angular rate of change, magnetic field strength, absolute position, speed, elevation, rate of elevation change, breathing rate, etc.) may be acquired by one or more processors via one or more sensors, such as a motion signal sensor. In embodiments, multiple motion signal sensors may be placed at various locations on and/or off the user's body for use in determining various aspects of user-motion and/or determining one or more aspects of movement associated with the activity in which the user is engaged. For example, three linear acceleration signals in substantially mutually perpendicular directions may be acquired using one or more motion signal sensors, such as a digital tri-axial accelerometer collocated with optics.

Motion signals acquired by a processor of the fitness monitor from one or more motion signal sensors may be analyzed by the processor to identify or determine one or more motion parameters of the fitness monitor (block 404). The motion parameters may include an intensity (i.e., magnitude) of one or more sources of motion and a frequency associated with each source of motion.

The processor of the fitness monitor may identify one or more motion signal frequencies by performing a variety of techniques. For example, the processor may perform spectral decomposition with a digital Fourier transform (DFT), spectral decomposition using banks of bandpass filters, autocorrelation, time-domain analysis (such as zero-crossing counting), or any other suitable techniques to determine a frequency associated with one or more motion signals. The processor may determine motion intensity by calculating a signal root mean square (RMS) power or signal peak-peak of the motion signal. In some configurations, the motion signal may be pre-conditioned with a bandpass filter before the motion signal is analyzed to determine a motion intensity and a frequency of one or more components of the motion signal.

Concurrently and/or consecutively, the fitness monitor may acquire a PPG signal (block 406). The fitness monitor may include one or more emitter drivers, such as LED drivers, configured to cause the one or more emitters, such as LEDs, to output light at one of a plurality of intensity levels. The one or more emitters are operable to output light toward the skin of the user. For instance, emitters may be positioned on the top or a bottom of a user's wrist (at a location where a watch housing typically rests when secured to the wrist of a user) and output light into the user's wrist.

The fitness monitor may further include a receiver, which may include one or more photodiodes and a photometric front end, configured to receive a reflection of the transmitted light from the user's skin and generate a light intensity signal based on the received reflection. The light intensity signal may be an analog signal that is filtered, processed and converted into a digital PPG signal by the photometric front end of the receiver. In embodiments, the light intensity signal is processed and digitized into a PPG signal by a processor of the fitness monitor directly or by controlling circuitry, such as the photometric front end.

It is to be understood that the photometric front end and the one or more emitter drivers may be integrated within the processor and the receiver includes one or more photodiodes. For example, in embodiments, the processor may include a photometric front end having features that attenuate the impact of ambient light on the light intensity signal provided by one or more photodiodes, improve the SNR of the light intensity signal, filter the light intensity signal and digitize the light intensity signal into the PPG signal for analysis. In other embodiments, the processor may be communicatively coupled with the photometric front end.

After the PPG signal has been acquired by the processor of the fitness monitor, the PPG signal may be filtered to attenuate (reduce) low and high frequency components thereof (block 408). For example, the PPG signal may be filtered with a bandpass filter that includes a passband that spans, at least, the frequency of a desired cardiac component fundamental frequency range. The frequency range may span cardiac component frequencies that are possible for any subject engaged in activities ranging from full rest to most intense activity. Thus, the processor may pre-condition the PPG signal by attenuating frequency components of the PPG signal below the frequency band that includes the cardiac component and/or attenuates frequency components above the frequency band that includes the cardiac component.

In embodiments, the processor may determine the frequency content of the pre-conditioned PPG signal by applying DFT techniques and/or use of linear bandpass filters (block 410). Specifically, the processor may perform a Fourier transform of the PPG signal, which was originally acquired in the time domain, to the frequency domain in order to determine one or more frequencies associated with one or more components of the PPG signal.

In embodiments, a bank of linear bandpass filters may be utilized to obtain a time-varying spectral decomposition with a high spectral resolution at a high refresh rate. The operating characteristics of the one or more filters of the filter bank may be different for different regions of the analyzed frequency spectrum. For example, the filter bandwidth may be different in different regions of the analyzed frequency spectrum, trading off spectral resolution for temporal resolution. The operating characteristics of the filter bank may change in time in response to certain events. For example, the processor may increase the bandwidth of the filters when the processor determines that the fitness monitor is in a rapidly changing user environment (e.g., the user starts running) to allow for a faster response, and the bandwidth of the filters may be decreased by the processor during substantially static periods of time to improve spectral resolution.

The processor may utilize spectral decomposition of the PPG signal to frequency domain to determine a frequency associated with a desired cardiac component and an undesired motion component and/or respiratory component of a PPG signal (block 414). Specifically, the processor may analyze the PPG signal after spectral decomposition to determine one or more frequencies associated with one or more components of the PPG signal to identify or determine a desired cardiac component, a motion component, which may be associated with motion parameters (e.g., a cadence of the user), and a respiratory component. For instance, the processor may use the determined spectral content of the PPG signal to identify dominant and/or temporally consistent spectral components (e.g., spectral peaks) of the PPG signal. The processor may identify individual spectral peaks as spectral regions of substantially higher spectral energy relative to other parts of the spectrum and then track identified spectral peaks from one time epoch to the next (block 414). Thus, the processor may identify and/or track multiple spectral peaks in any time epoch to form a set of tracked spectral peaks. In embodiments, motion parameters determined based on an identified motion component in the frequency domain (block 414) may communicated to the user on a display.

Additionally and/or alternatively, the processor may identify information (block 416) about the components of the PPG signal, which includes a desired cardiac component, an undesired motion component and a respiratory component, and the motion signal by analyzing the dominant and/or temporally consistent spectral components (e.g., spectral peaks) of the PPG signal identified in the frequency domain (block 414) with the motion signal generated by an inertial sensor based on sensed movement (block 404). For example, the processor may analyze a set of spectral speaks with a set of heuristics to select or identify, from amongst a plurality of spectral peaks, a spectral component determined to correspond to the desired cardiac component of the PPG signal (block 416).

The heuristics applied by the processor during component identification (block 416) may include one or more suitable techniques. For example, spectral components corresponding to one or more motion components within the PPG signal may be identified by the processor from amongst the spectral peaks within the PPG signal by comparing the frequencies of spectral peaks to the frequency of the motion signal and the harmonics of the motion signal (block 404). In embodiments where breathing rate is measured or estimated by other sensors, spectral components corresponding to one or more respiratory components within the PPG signal may be identified by the processor from amongst the spectral peaks within the PPG signal by comparing the frequencies of spectral peaks to the breathing rate and the harmonics of the breathing rate (block 404).

Similarly, in embodiments, the processor may isolate a respiratory component of the PPG signal and determine a breathing rate of the user based on the isolated respiratory component. For example, one or more spectral components of the PPG signal, from amongst the plurality of spectral peaks of the PPG signal, may correspond to a respiratory component and the processor may identify one or more spectral peaks of the PPG signal corresponding to the respiratory component by comparing the determined spectral peaks of the PPG signal (block 414) to undesired components of the PPG signal. The processor may then isolate the respiratory component by configuring the time-variant filters with filter coefficients corresponding to the undesired components of the PPG signal, such as the cardiac component, the motion component and/or the respiratory component, to isolate the desired respiratory component.

In yet another example, undesired spectral components of the PPG signal may be identified by the processor in a plurality of spectral peaks identified in the frequency domain after spectral decomposition of the PPG signal (block 414), and the processor may identify and exclude those spectral peaks from consideration as peaks possibly corresponding to the desired cardiac component of the PPG signal (block 416). The processor may reduce the probability of identifying such spectral peaks that do not correspond to the cardiac component of the PPG signal by identifying components of the PPG signal (block 416).

The processor may also identify time periods when the frequency of the desired cardiac component of the PPG signal approaches and overlaps frequencies of other components of the PPG signal that have been identified by the processor as not corresponding to the cardiac component of the PPG signal (block 416). As a result, the processor may determine that the frequency of the cardiac component of the PPG signal is approaching the frequency of a motion component of the PPG signal (block 414), which may be confirmed by the processor as the frequency of the motion signal provided by the inertial sensor (block 404).

In some embodiments, the processor may utilize a model stored in memory for a PPG signal, a desired cardiac component of the PPG signal, undesired motion components of the PPG signal, a respiratory component of the PPG signal, as well as other components of the PPG signal. The stored model may include static factors corresponding to a predetermined probability of the cardiac component of the PPG signal having one or more frequencies. For example, the memory may store, and the processor may utilize, a model having a fundamental frequency range associated with a cardiac component of a PPG signal. The processor may use the stored fundamental frequency range of the cardiac component to determine that frequencies at the upper and/or lower end of the fundamental frequency range may be less likely to be associated with the cardiac component of the PPG signal than frequencies well within the upper and lower ends of the fundamental frequency range.

In embodiments, the processor may also determine and utilize dynamic factors to determine a probability of one or more frequencies being associated with the desired cardiac component of the PPG signal. For example, the processor may determine that the distribution of human cardiac cycle frequencies is higher during periods of high motion intensity than during periods of low motion intensity based on a determined frequency of a motion signal, a determined intensity of the motion signal, a frequency of a motion component of the PPG signal, a determined intensity of the motion component of the PPG signal, a determined intensity of a respiratory component of the PPG signal, a frequency of the respiratory component of the PPG signal, and a determined activity type.

The processor may determine, and the memory may store, a model for the cardiac component of the PPG signal based on a statistical characterization of recently identified cardiac components of PPG signals to determine (and subsequently modify) the likelihood that a frequency of a component of the PPG signal corresponds to the cardiac component of the PPG signal. The processor may determine whether PPG signals presently being provided by and received from the receiver include a cardiac component based on the stored model. For example, the processor may calculate the mean and the standard deviation of the recently passed cardiac cycle frequencies and use this information to assign a probability to any given frequency that this frequency corresponds to the cardiac component of the PPG signal.

The processor may also adapt stored metrics used to identify a cardiac component of the PPG signal over time to the user of the fitness monitor by determining a user-specific model based on data from various sensors that may be used by the processor or determine one or more relationships between a cardiac component of the PPG signal (heartbeat signal) and various physical events resulting in movement of the fitness monitor. The processor may implement Kalman filtering techniques in some configurations to filter and/or estimate the frequency of the cardiac, motion and/or respiratory components of the PPG signal.

A time-domain post-condition module (block 418) may be configured by the processor to filter the pre-conditioned PPG signal or the PPG signal (without pre-conditioning bypassing block 408) to remove one or more components of the PPG signal to isolate the desired cardiac component of the PPG signal (block 418). The time-domain post-condition module (block 418) includes one or more time-variant filters to perform the removal of PPG signal components included or interfering with the desired cardiac component of the PPG signal. It is to be understood that the time-domain post-condition module, including the time-variant filters, may be integrated within the processor.

The processor may configure one or more time-variant filters of the time-domain post-condition module to isolate the cardiac component of the PPG signal from other components of the PPG signal. The time-variant filters may be a combination of any time-variant filters including, for example, one or more of time-variant bandpass filters, time-variant notch (or bandstop) filters, time-variant low-pass filters and/or time-variant high-pass filters. The time-variant filters may be a combination of finite-impulse-response (FIR) filters and infinite-impulse-response (IIR) filters.

The processor may configure one or more time-variant filters that receive a PPG signal (with or without time-domain pre-conditioning) with determined filter coefficients to isolate the cardiac component of the PPG signal from other components of the PPG signal. In embodiments, the processor may configure the time-variant filter with the determined filter coefficients and filter, in the time domain via the time-variant filter, the identified motion component from the PPG signal to isolate the cardiac component.

The processor may analyze a portion of the PPG signal received during a first period of time to identify a motion or cardiac component and then configure one or more time-variant filters that receive a PPG signal with determined filter coefficients to isolate the cardiac component of the PPG signal from other components of the PPG signal. For example, the processor may determine one or more frequencies associated with the motion signal and the PPG signal provided during a first time period, identify the motion component in the PPG signal for the first time period based on the determined one or more frequencies of the motion signal and filter, via one or more time-variant filters, the identified motion component from the PPG signal provided during a second time period to isolate the cardiac component of the PPG signal for the second time period. Similarly, the processor may determine one or more frequencies associated with the motion signal and the PPG signal provided during a first period, identify the cardiac component in the PPG signal for the first time period based on the determined one or more frequencies of the motion signal and the PPG signal, and filter, via one or more time-variant filters, the PPG signal provided for a second time to isolate the cardiac component of the PPG signal for the second time period based on the identified cardiac component for the first time period.

In embodiments, the first and second time periods correspond to the same period of time. In other words, the processor may filter an identified motion or cardiac component from the same instance of a PPG signal that was analyzed to identify the motion component or cardiac component. For example, the processor may identify a motion component in the PPG signal for a time period and filter, via the time-variant filter, the identified motion component from the PPG signal provided during that time period to isolate the cardiac component of the PPG signal for a time period of interest. Similarly, the processor may identify a cardiac component in the PPG signal for a time period and filter, via the time-variant filter, the PPG signal provided for a second time to isolate the cardiac component of the PPG signal for the second time period based on the identified cardiac component for a time period of interest.

The processor may determine filter coefficients based on an identified cardiac, motion component and/or respiratory component in the PPG signal for the first time period and configure the one or more time-variant filters with the determined filter coefficients.

Once the pre-conditioned PPG signal from the time-domain pre-conditioning module (block 408) is spectrally decomposed by the processor into a frequency-domain representation of the PPG signal, the processor may use the frequency-domain representation to determine information in the component identification module and one or more filter coefficients based on the determined information (block 416). The filter coefficients may be determined upon each occurrence of the cardiac component being identified based on the determined one or more frequencies of the motion signal and the transformed PPG signal. The processor may configure the time-variant filter with the determined filter coefficients upon each occurrence of the cardiac component being identified.

The filter coefficients may be determined by the processor based on the identified motion component, cardiac component or respiratory component in a PPG signal for a first time period and configure the time-variant filter with the determined filter coefficients. The cardiac component of the PPG signal for a second time period (i.e., a newly received PPG signal) may be isolated continuously based on current configurations of filter coefficients within the time-variant filters determined by the processor based on the cardiac component of the PPG signal for a first time period (block 416).

Frequency bands identified by the processor to contain components other than the desired cardiac component of the PPG signal, such as the motion and respiratory components of the PPG signal, may be identified by the component identification module (block 416) and one or more of those frequency bands may be attenuated in the time-domain post-condition module (block 418) based on filter coefficients determined by the processor for each occurrence of the cardiac and/or other components being identified by the processor.

The processor may control or perform the filtering of components other than the desired cardiac component of the PPG signal using the time-domain post-condition module (block 418) based on any applicable information, such as frequency information determined by the component identification module (block 416). For example, the PPG signal may be notch-filtered to selectively attenuate cyclical motion components and/or cyclical respiratory component within the PPG signal to isolate the cardiac and/or respiratory components of the PPG signal. Additionally or alternatively, the processor may utilize a bandpass filter around the cardiac component of the PPG signal (i.e., removing signal components above and below the permitted band) to isolate the cardiac component of the PPG signal from other components of the PPG signal.

The processor may determine one or more filter coefficients based on the identified cardiac component and/or other sources within the PPG signal. The processor may configure one or more time-variant filters of the time-domain post-condition module (block 418) with filter coefficients determined by the processor to isolate the desired cardiac component of the PPG signal from other components of the PPG signal. For example, the processor may configure a time-variant bandstop filter with filter coefficients to implement a bandstop filter with a stopband inclusive of frequencies associated with undesired PPG signal components, which may include the motion and respiratory components of the PPG signal. Similarly, a plurality of time-variant bandstop filters may be configured by the processor with determined filter coefficients to isolate the cardiac component of the PPG signal by removing frequencies associated with a plurality of undesired PPG signal components, including the motion and respiratory components of the PPG signal.

The processor may determine the filter coefficients based on information determined in the component identification module (block 416). For example, the processor may periodically reconfigure the time-variant filter based on the cardiac component identified in the frequency domain. The processor may subsequently change the determined filter coefficients used to configure the time-variant filters of the time-domain post-condition module (block 418) over time based on new information determined in the component identification module as current PPG signals and motion signals are acquired and analyzed by the processor. The processor may periodically (e.g., every 2 seconds) configure the one or more time-variant filters of the time-domain post-condition module (block 418) based on information determined in the component identification module (block 416).

In embodiments, the processor may use the identified cardiac component of the PPG signal to configure the one or more time-variant filters of the time-domain post-condition module (block 418). A determined frequency associated with the cardiac component of the PPG signal may be used to determine a filter coefficient and configure one or more time-variant filters with the determined filter coefficient.

For example, the processor may configure a time-variant bandpass filter, at a first operating period or time, with filter coefficients to implement a bandpass filter with a first center frequency approximately equal to a first fundamental frequency of the cardiac component of the PPG signal as identified by the component identification module (block 416) and configure the time-variant filter, at a second operating period or time, with filter coefficients to implement a bandpass filter with a second center frequency approximately equal to a second fundamental frequency of the cardiac component. Additionally, the processor may configure the time-variant bandpass filter with determined filter coefficients to implement a bandpass filter with a passband that is substantially inclusive of the fundamental and/or harmonic frequencies contained within the cardiac component of the PPG signal, but possibly exclusive of frequencies containing sources of interference, such as the motion and respiratory components of the PPG signal.

Filter coefficient sets stored in memory may be pre-calculated for combinations of identified components of the PPG signal and parameters. For example, the filter coefficient sets may be organized as a look-up table including predetermined filter coefficients for various parameters of components of the PPG signal (e.g., frequency of cardiac component of PPG signal, frequency of motion component of PPG signal, frequency of the respiratory component of the PPG signal, etc.) that may be identified during use of the fitness monitor during physical activities. The processor may then retrieve the filter coefficient sets from memory based on identified components of the PPG signal and/or other parameters and configure the one or more time-variant filters with the retrieved filter coefficients.

Further, processor may adjust the determined filter coefficients used to configure the time-variant filters by making use of information about the frequency content of the cardiac component of the PPG signal as provided by any source within or outside the fitness monitor. For example, information stored in memory regarding one or more frequency bands typically containing energy of the cardiac signal component may be used by the processor to determine a filter coefficient. Alternatively, the processor may use information about the approximate frequency-spectral locations of one or more bands substantially containing energy of the cardiac signal component to determine a filter coefficient.

The processor may analyze the cardiac component of the PPG signal provided at the output of the time-domain post-condition module (block 418) to measure one or more physiological characteristics based on the cardiac component of the PPG signal. The processor may analyze the cardiac component to determine one or more performance characteristics (e.g., metrics, statistics, etc.) for the user. For example, performance characteristics may be calculated on a set of data constituting the times between the same features in successive cycles of the cardiac component, over a period of time.

The processor may analyze the post-conditioned PPG signal in the time domain in the heartbeat identification module (block 420) to identify the user's heartbeat and precise moments associated with each heartbeat. The frequency of the cardiac component of the PPG signal may then be readily determined by the processor based on a time difference between two consecutive heartbeat moments. For example, the processor may determine times of zero-crossings of the post-conditioned PPG signal as heartbeat times. For example, the time between similar or same features in successive cycles of the cardiac component is measured, such as measuring the time between successive cycle peaks or cycle troughs. Likewise, the time between successive positive-going or negative-going zero crossings may be measured.

In some embodiments, heart-rate variability (HRV) is calculated by the processor using a set of data including the times between successive positive-going or negative-going zero crossings of the cardiac component. One of a number of known techniques may be used to perform heart-rate variability calculation based on the data that include the times between the same features in successive cycles of the cardiac component. That is, data including time differences between two consecutive heartbeat moments generated by the heartbeat identification module (block 420), over a period of time, may be utilized to calculate the heart-rate variability value (block 422). The processor may also analyze the cardiac component of the PPG signal to determine stress (block 424), recovery time (block 426), VO2 max (block 628), and/or sleep quality of the user (block 430).

In embodiments, the processor may control the display to output a frequency of the spectral peak determined by the processor corresponding to the cardiac component of the PPG signal in the component identification module (block 416) as the user's heart rate, which may correspond frequency of the cardiac component of the PPG signal. In embodiments, the processor may use a combination of the frequency of the cardiac component of the PPG signal determined by the component identification module (block 416) and the frequency of the cardiac component of the PPG signal determined by the heartbeat identification module (block 420) to generate a heart-rate for the user. For example, the processor may use the frequency of the cardiac component of the PPG signal determined by the component identification module (block 416) as the user's heart rate when the processor determines a changing use case (varying between activity types). Similarly, the processor may use the frequency of the cardiac component of the PPG signal determined by the heartbeat identification module (block 420) when the processor determines a substantially static use application. This may allow the output heart rate to be responsive during times of rapid change.

In embodiments, the processor may aide the user with placement of the fitness monitor on the body with a gauge indicating the signal strength based on the determined cardiac component of the PPG signal from the output of the time-domain post-condition module (block 418). In one configuration, the cardiac-cycle signal-strength gauge is a bar graph viewable on the system display indicating the strength of the detected cardiac component of the PPG signal after filtering of the PPG signal in the time-domain post-condition module (block 418). In other configurations, the cardiac-cycle signal-strength gauge is a numeric value presented on a display of the fitness monitor. In general, any means capable of conveying information to the user, including sound, vibration, LCD, LED and the like may be used to indicate to the user information corresponding to the quality and/or strength of the cardiac component of the PPG signal. The user may then use the gauge to choose an optimal location for the fitness monitor on the user's body (e.g., precise location on the user's wrist). For example, the user may choose to position the fitness monitor such that the photodiode is positioned at the top of the wrist, or the bottom of the wrist. The user may also choose to move the fitness monitor and the photodiode axially along the user's arm to optimize signal strength of the cardiac component of the PPG signal. The user may also adjust the tightness (pressure/force) of the fitness monitor causing the photodiodes to be pressed against the skin (by, for example, adjusting tightness of a band of the fitness monitor) to achieve best signal strength of the cardiac component of the PPG signal.

The signal strength of the cardiac component may be quantified by calculating the peak to peak (dynamic range) of the PPG signal while the user is stationary. However, the cardiac component signal strength may be quantified using any number known metrics such as RMS of the PPG signal or the SNR of the cardiac component within the PPG signal. Depending on the method chosen for the quantification of the cardiac component signal strength, the measurement may be performed while the user is stationary or engaged in an activity. The cardiac component signal strength may be recorded during an activity to augment subsequent analysis and/or display of other metrics extracted from the PPG signal.

An example embodiment of a fitness monitor 500 capable of executing the methods and processes described above is illustrated in FIG. 5. The fitness monitor 500 includes a user interface module 502, a location determining component 504 (e.g., a global positioning system (GPS) receiver, Assisted-GPS, etc.), a communication module 506, an inertial sensor 508 (e.g., accelerometer, gyroscope, etc.), and a controller 510. The fitness monitor 500 may also implement techniques implemented by a photometric front end circuit, an optical sensing module and application processor, as described in simultaneously filed U.S. patent application Ser. No. 15/296,938, entitled, "SYSTEM AND METHOD FOR GENERATING A PPG SIGNAL"; the contents of which are expressly incorporated herein by reference.

Figure 5:
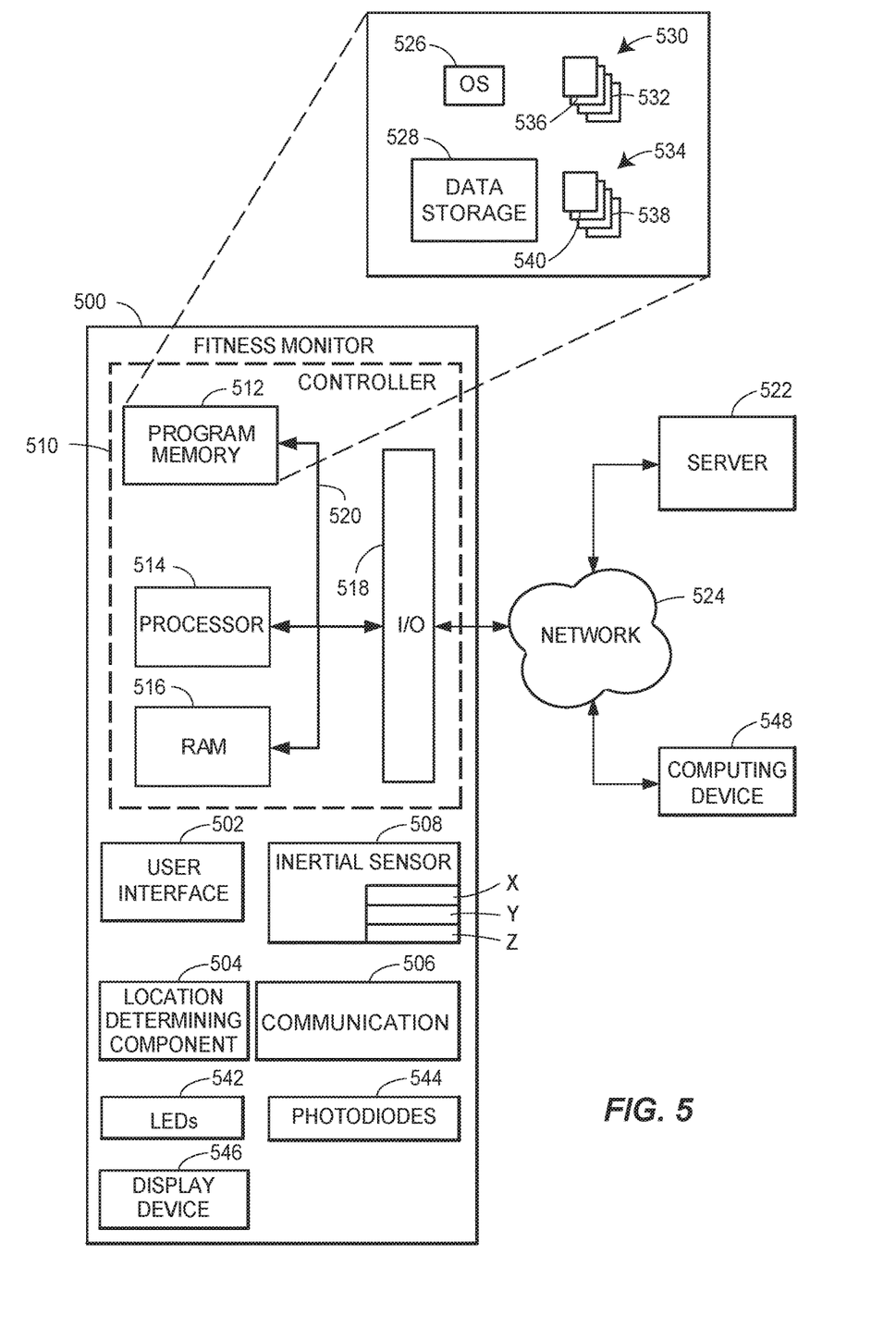
FIG. 5 is a block diagram of an example embodiment of a fitness monitor for monitoring a physiological characteristic of a user as described herein.

The fitness monitor 500 may be a general-use wearable computer (e.g., a watch, smart glasses, etc.), a cellular phone, a smartphone, a tablet computer, or a mobile personal computer, capable of monitoring a physiological aspect of an individual as described herein. The fitness monitor 500 may be a thin-client device or terminal that sends processing functions to a server device 522 via a network 524. Communication via the network 524 may include any combination of wired and wireless technology. For example, network 524 may include a USB cable between fitness monitor 500 and computing device 548 to facilitate the bi-directional transfer of data between fitness monitor 500 and computing device 548.

The controller 510 may include a program memory 512, a microprocessor (MP) 514, a random-access memory (RAM) 516, and an input/output (I/O) circuitry 518, all of which may be communicatively interconnected via an address/data bus 520. Although the I/O circuitry 518 is depicted in FIG. 5 as a single block, the I/O circuitry 518 may include a number of different types of I/O circuits. The program memory 512 may include an operating system 526, a data storage device 528, a plurality of software applications 530, and/or a plurality of software routines 534. The operating system 526 of program memory 512 may include any of a plurality of mobile platforms, such as the iOS®, Android™, Palm® webOS, Windows® Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. The data storage device 528 of program memory 512 may include application data for the plurality of applications 530, routine data for the plurality of routines 534, and other data necessary to interact with the server 522 through the network 524. In particular, the data storage device 528 may include cardiac component data associated with the individual and/or one or more other individuals. The cardiac component data may include one or more compilations of recorded physiological aspects of the user, including, but not limited to, a heartbeat, heart rate, heart-rate variability, speed, distance traveled, calculating calories burned, body temperature, and the like. In some embodiments, the controller 510 may also include, or otherwise be operatively coupled for communication with other data storage mechanisms (e.g., one or more hard disk drives, optical storage drives, solid state storage devices, etc.) that may reside within the fitness monitor 500 and/or operatively coupled to the network 524 and/or server device 522.

The fitness monitor 500 also includes one or more emitters, such as LEDs 542, that output visible and/or non-visible light and one or more receivers (e.g., photodiodes) of visible and/or non-visible light that generate a light intensity signal based on the received electromagnetic radiation. For example, LEDs 542 may include any combination of green light-emitting diodes (LEDs), red LEDs, and/or infrared LEDs that emit light into the user's skin.

The fitness monitor 500 also includes one or more photodiodes 544 capable of receiving reflections of visible-light and/or infrared (IR) light output by the LEDs 542 into the user's skin and generating a light intensity signal based on the received reflection. The light intensity signals generated by the one or more photodiodes 544 may be communicated to a photometric front end for signal processing and digitization. The photometric front end may include filters for the light intensity signals and analog-to-digital converters to digitize the light intensity signals into PPG signals including a cardiac signal component associated with the user's heartbeat.

Typically, the one or more LEDs 542 are positioned against the user's skin to emit light into the user's skin and the one or more photodiodes 544 are positioned near the LEDs 542 to receive light emitted by the one or more emitters after reflection from the user's skin. The processor of 514 of fitness monitor 500 may determine a PPG signal based on a light intensity signal output by one or more photodiodes 544 based on light reflected after transmission of the light through or reflection from the user's skin that has been received by the photodiodes 544.

In both the transmitted and reflected uses, the intensity of measured light may be modulated by the cardiac cycle due to variation in tissue blood perfusion during the cardiac cycle. In activity environments, the intensity of measured light may also be strongly influenced by many other factors, including, but not limited to, static and/or variable ambient light intensity, body motion at the measurement location, static and/or variable sensor pressure on the skin, motion of the sensor relative to the body at the measurement location, breathing, and/or light barriers (including hair, opaque skin layers, sweat, etc.). Relative to these sources, the cardiac cycle component of the PPG signal can be very weak, frequently by one or more orders of magnitude.

The location determining component 504 may be a GPS receiver that is configured to provide geographic location information of the fitness monitor 500. The location determining component may be, for example, a GPS receiver such as those provided in various products by GARMIN®. Generally, GPS is a satellite-based radio navigation system capable of determining continuous position, velocity, time, and direction information. Multiple users may simultaneously utilize GPS. GPS incorporates a plurality of GPS satellites that orbit the earth. Based on these orbits, GPS satellites can relay their location to a GPS receiver. For example, upon receiving a GPS signal, e.g., a radio signal, from a GPS satellite, the fitness monitor 500 disclosed herein can determine a location of that satellite. The fitness monitor 500 can continue scanning for GPS signals until it has acquired a number, e.g., at least three, of different GPS satellite signals. The fitness monitor 500 may employ geometrical triangulation, e.g., where the watch utilizes the known GPS satellite positions to determine a position of the fitness monitor 500 relative to the GPS satellites. Geographic location information and/or velocity information can be updated, e.g., in real time on a continuous basis, for the fitness monitor 500.

In embodiments, inertial sensor 508 may incorporate one or more accelerometers positioned to determine the acceleration and direction of movements of fitness monitor 500. The accelerometer may determine magnitudes of acceleration in an X-axis, a Y-axis, and a Z-axis to measure the acceleration and direction of movement of fitness monitor 500 in each respective direction (or plane). It will be appreciated by those of ordinary skill in the art that a three dimensional vector describing a movement of the fitness monitor 500 through three dimensional space can be established by combining the outputs of the X-axis, Y-axis, and Z-axis accelerometers using known methods. Single and multiple axis models of the inertial sensor 508 are capable of detecting magnitude and direction of acceleration as a vector quantity, and may be used to sense orientation and/or coordinate acceleration of the user.

The photodiodes 544, location determining component 504 and the inertial sensors 508 may be referred to collectively as the "sensors" of the fitness monitor 500. It is also to be appreciated that additional location determining components 504 and/or inertial sensor(s) 508 may be operatively coupled to the fitness monitor 500. In embodiments, the fitness monitor 500 may also include or be coupled to a microphone incorporated with the user interface module 502 and used to receive voice inputs from the user while the fitness monitor 500 monitors a cardiac signal of a user and determines physiological information based on the cardiac signal.

The communication module 506 may communicate with computing device 548 and/or server device 522 via any suitable wired or wireless communication protocol independently or using I/O circuitry 518. The wired or wireless network 524 may include a wireless telephony network (e.g., GSM, CDMA, LTE, etc.), one or more standard of the Institute of Electrical and Electronics Engineers (IEEE), such as 802.11 or 802.16 (Wi-Max) standards, Wi-Fi standards promulgated by the Wi-Fi Alliance, Bluetooth standards promulgated by the Bluetooth Special Interest Group, a near field communication standard (e.g., ISO/IEC 18092, standards provided by the NFC Forum, etc.), and so on. Wired communications are also contemplated such as through universal serial bus (USB), Ethernet, serial connections, and so forth.

The fitness monitor 500 may be configured to communicate via one or more networks 524 with a cellular provider and an Internet provider to receive mobile phone service and various content, respectively. Content may represent a variety of different content, examples of which include, but are not limited to: map data, which may include route information; web pages; services; music; photographs; video; email service; instant messaging; device drivers; real-time and/or historical weather data; instruction updates; and so forth.

The user interface 502 of the fitness monitor 500 may include a "soft" keyboard that is presented on a display screen of the fitness monitor 500, an external hardware keyboard communicating via a wired or a wireless connection (e.g., a Bluetooth keyboard), and/or an external mouse, or any other suitable user-input device or component. As described earlier, the user interface 502 may also include or communicate with a microphone capable of receiving voice input from a vehicle operator as well as a display device 546 having a touch input.

With reference to the controller 510, it should be appreciated that controller 510 may include multiple microprocessors 514, multiple RAMs 516 and multiple program memories 512. The controller 510 may implement the RAM 516 and the program memories 512 as semiconductor memories, magnetically readable memories, and/or optically readable memories, for example. The one or more processors 514 may be adapted and configured to execute any of the plurality of software applications 530 and/or any of the plurality of software routines 534 residing in the program memory 512, in addition to other software applications. One of the plurality of applications 530 may be a client application 532 that may be implemented as a series of machine-readable instructions for performing the various functions associated with implementing the performance monitoring system as well as receiving information at, displaying information on, and transmitting information from the fitness monitor 500. The client application 532 may function to implement a system wherein the front-end components communicate and cooperate with back-end components as described above. The client application 532 may include machine-readable instructions for implementing the user interface 502 to allow a user to input commands to, and receive information from, the fitness monitor 500. One of the plurality of applications 530 may be a native web browser 536, such as Apple's Safari®, Google Android™ mobile web browser, Microsoft Internet Explorer® for Mobile, Opera Mobile™, that may be implemented as a series of machine-readable instructions for receiving, interpreting, and displaying web page information from the server device 522 or other back-end components while also receiving inputs from the fitness monitor 500. Another application of the plurality of applications 530 may include an embedded web browser 542 that may be implemented as a series of machine-readable instructions for receiving, interpreting, and displaying web page information from the server device 522 or other back-end components within the client application 532.

The client applications 530 or routines 534 may include an accelerometer routine 538 that determines the acceleration and direction of movements of the fitness monitor 500, which correlate to the acceleration, direction, and movement of the user. The accelerometer routine 538 may receive and process data from the inertial sensor 508 to determine one or more vectors describing the motion of the user for use with the client application 532. In some embodiments where the inertial sensor 508 includes an accelerometer having X-axis, Y-axis, and Z-axis accelerometers, the accelerometer routine 538 may combine the data from each accelerometer to establish the vectors describing the motion of the user through three dimensional space. In some embodiments, the accelerometer routine 538 may use data pertaining to less than three axes.

The client applications 530 or routines 534 may further include a velocity routine 540 that coordinates with the location determining component 504 to determine or obtain velocity and direction information for use with one or more of the plurality of applications, such as the client application 532, or for use with other routines.

The user may also launch or instantiate any other suitable user interface application (e.g., the native web browser 536, or any other one of the plurality of software applications 530) to access the server device 522 to implement the monitoring process. Additionally, the user may launch the client application 532 from the fitness monitor 500 to access the server device 522 to implement the monitoring process.

After data has been gathered or determined by the sensors of the fitness monitor 500, previously acquired data may be utilized to determine the extent of adjustment to the time-variant filters. Once the extent of the adjustment has been assessed, a cardiac signal can be determined. The fitness monitor 500 may also transmit information associated with the cardiac component of the user. For example, the transmitted information may be sent to a fitness facility capable of analyzing the data.

In embodiments where the fitness monitor 500 is a thin-client device, the server device 522 may perform one or more processing functions remotely that may otherwise be performed by the fitness monitor 500. In such embodiments, the server device 522 may include a number of software applications capable of receiving user information gathered by the sensors to be used in determining the cardiac component of the user. For example, the fitness monitor 500 may gather information from its sensors as described herein, but instead of using the information locally, the fitness monitor 500 may send the information to the server device 522 for remote processing. The server device 522 may perform the analysis of the gathered user information to determine a fitness aspect of the user as described herein. The server device 522 may also transmit information associated with the cardiac component of the user. For example, the information transmitted by the server device 522 may be sent to a fitness facility and include a request for analysis.

Figure 6A:
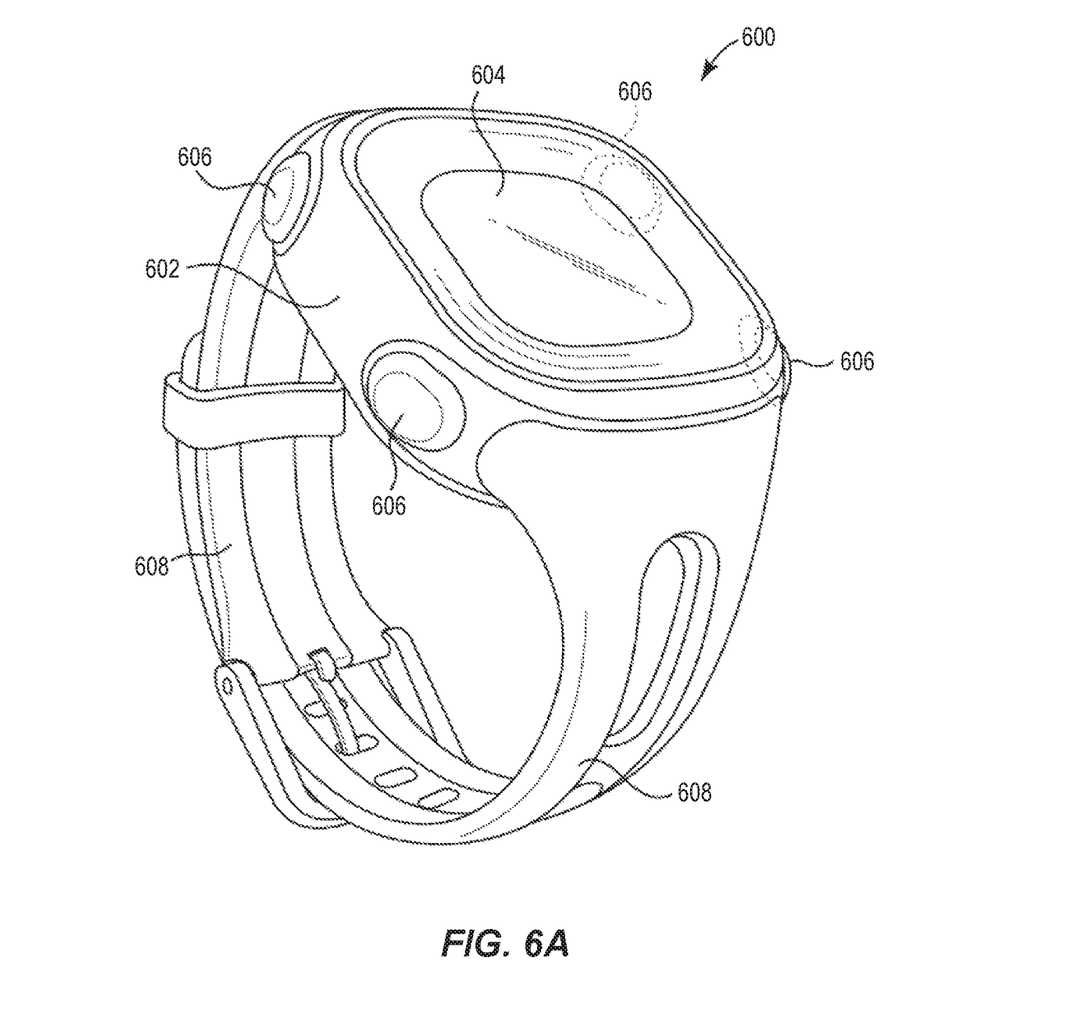
FIGS. 6A and 6B are illustrations depicting one embodiment of the fitness monitor for monitoring one or more physiological and/or performance characteristics of a user as described herein.
Figure 6B:
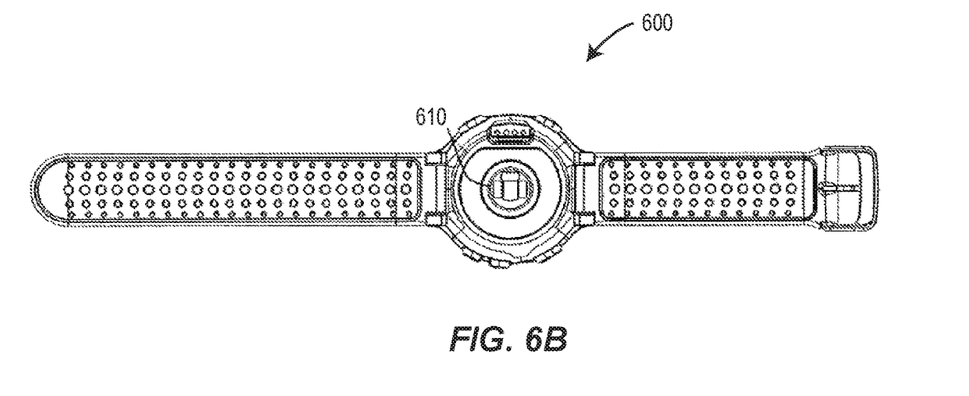

FIGS. 6A and 6B illustrate views of one example embodiment of the fitness monitor in accordance with one or more aspects described herein. The fitness monitor 600 described above may be configured in a variety of ways to determine and provide fitness information, including one or more cardiac components, as well as navigation functionality to the user of the device 600. For instance, fitness monitor 600 includes a housing 602 of a sports watch or a pedometer including a processor configured for use during fitness and/or sporting activities. It is contemplated, however, that the disclosed techniques may be implemented in a mobile phone, a hand-held portable computer, a tablet computer, a personal digital assistant, a multimedia device, a media player, a game device, any combination thereof, and so forth.

The fitness monitor 600 includes a case or housing 602 configured to house, e.g., substantially enclose, various components of the fitness monitor 600. The housing 602 may be formed from a lightweight and impact-resistant material such as plastic, nylon, or combinations thereof, for example. The housing 602 may be formed from a non-conductive material, such a non-metal material, for example. The housing 602 may include one or more gaskets, e.g., a seal, to make it substantially waterproof or water resistant. The housing 602 may include a location for a battery and/or another power source for powering one or more components of the fitness monitor 600. The housing 602 may be a singular piece or may include a plurality of sections. In some embodiments, the housing 602 may be formed from a conductive material, such as metal, or a semi-conductive material.

The fitness monitor 600 includes a display device 604. The display device 604 may include a liquid crystal display (LCD), a thin film transistor (TFT), a light-emitting diode (LED), a light-emitting polymer (LEP), and/or a polymer light-emitting diode (PLED). The display device 604 may be capable of displaying text and/or graphical information. The display device 604 may be backlit such that it may be viewed in the dark or other low-light environments. One example embodiment of the display device 604 is a 100 pixel by 64 pixel film compensated super-twisted nematic display (FSTN) including a bright white light-emitting diode (LED) backlight. The display device 604 may include a transparent lens that covers and/or protects components of the fitness monitor 600. The display device 604 may be provided with a touch screen to receive input (e.g., data, commands, etc.) from a user. For example, a user may operate the fitness monitor 600 by touching the touch screen and/or by performing gestures on the screen. In some embodiments, the touch screen may be a capacitive touch screen, a resistive touch screen, an infrared touch screen, combinations thereof, and the like. The fitness monitor 600 may further include one or more input/output (I/O) devices (e.g., a keypad, buttons, a wireless input device, a thumbwheel input device, a trackstick input device, and so on). The I/O devices may include one or more audio I/O devices, such as a microphone, speakers, and so on.

In accordance with one or more embodiments of the present disclosure, the fitness monitor 600 includes a user interface with one or more control buttons 606. As illustrated in FIG. 6A, four control button 606 are associated with, e.g., adjacent, the housing 602. While FIG. 6A illustrates four control buttons 606 associated with the housing 602, it is to be understood that the fitness monitor 600 may include more or less control buttons 606. Each control button 606 is configured to generally control a function of the fitness monitor 600. Functions of the mobile electronic device 600 may be associated with a location determining component and/or a performance monitoring component. Functions of the fitness monitor 600 may include, but are not limited to, displaying a current geographic location of the fitness monitor 600, mapping a location on the display 604, locating a desired location and displaying the desired location on the display 604, and presenting information based on a cardiac component of the PPG signal including, but not limited to, a cardiac cycle signal, a heartbeat signal, a heart-rate signal or variability of a heart rate signal for the user. User input may be provided from movement of the housing 602, for example, an inertial sensor(s), e.g., accelerometer, may be used to identify vertical, horizontal, and/or angular movement of the housing 602. In addition or alternately, user input may be provided from touch inputs identified using various touch sensing technologies, such as resistive touch or capacitive touch interfaces.

The fitness monitor 600 also includes an optical sensing module 610, as shown in FIG. 6B, including one or more emitters (e.g., LEDs) of visible and/or non-visible light and one or more receivers (e.g., photodiodes) of visible and/or non-visible light that generate a light intensity signal based on the received reflection of light.

The fitness monitor 600 includes a strap 608 that enables one or more LEDs and one or more photodiodes to be securely placed against the skin of a user. The strap 608 is associated with, e.g., coupled to and/or integrated with, the housing 602 and may be removably secured to the housing 602 via attachment of securing elements to corresponding connecting elements. Some examples of securing elements and/or connecting elements include, but are not limited to, hooks, latches, clamps, snaps, and the like. The strap 608 may be made of a lightweight and resilient thermoplastic elastomer and/or a fabric, for example, such that the strap 608 may encircle a portion of a user without discomfort while securing the fitness monitor to the user. The strap 608 may be configured to attach to various portions of a user, such as a user's leg, waist, wrist, forearm, and/or upper arm.

The applications and benefits of the systems, methods, and techniques described herein are not limited to only the above examples. Many other applications and benefits are possible by using the systems, methods, and techniques described herein. Thus, many modifications and variations may be made in the techniques and structures described and illustrated herein without departing from the spirit and scope of the present invention. Accordingly, it should be understood that the methods and apparatus described herein are illustrative only and are not limiting upon the scope of the invention.

It should also be understood that, unless a term is expressly defined in this patent using the sentence "As used herein, the term ' ' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Also, unless a claim element is defined by reciting the word "means" and a function without the recital of any structure, it is not intended that the scope of any claim element be interpreted based on the application of 35 U.S.C. §112(f) and/or pre-AIA 35 U.S.C. §112, sixth paragraph.

Moreover, although the foregoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

What is claimed is:

1. A fitness monitor for monitoring a cardiac signal of a user, the device comprising:
    an emitter configured to transmit light toward skin of the user;
    a receiver configured to receive a reflection of the transmitted light and provide a photoplethysmogram (PPG) signal based on the received reflection of the transmitted light, the PPG signal including a cardiac component and a motion component;
    an inertial sensor configured to provide a motion signal based on sensed movement of the fitness monitor;
    a time-variant filter configured to isolate a component of the PPG signal based on filter coefficients corresponding to a desired component of the PPG signal, and
    a processor coupled to the emitter, the receiver, the inertial sensor and the time-variant filter, the processor configured to:
        determine one or more frequencies associated with the motion signal;
        transform the PPG signal to the frequency domain;
        identify, in the frequency domain, the cardiac component in the PPG signal based on the determined one or more frequencies of the motion signal and the transformed PPG signal;
        determine filter coefficients based on the identified cardiac component in the PPG signal;
        configure the time-variant filter with the determined filter coefficients;
        filter, in the time domain via the time-variant filter, the motion component from the PPG signal to isolate the identified cardiac component; and
        calculate, in the time domain, the time between successive cycles of the isolated cardiac component of the PPG signal.

2. The fitness monitor of claim 1, wherein the time-variant filter is integrated within the processor.

3. The fitness monitor of claim 1, wherein the filter coefficients are determined upon each occurrence of the cardiac component being identified based on the determined one or more frequencies of the motion signal and the transformed PPG signal.

4. The fitness monitor of claim 3, wherein the processor configures the time-variant filter with the determined filter coefficients upon each occurrence of the cardiac component being identified.

5. The fitness monitor of claim 1, wherein the processor is further configured to periodically reconfigure the time-variant filter based on the cardiac component identified in the frequency domain.

6. The fitness monitor of claim 1, further comprising a bandpass filter, wherein the processor is further configured to configure the bandpass filter to pre-condition the PPG signal by attenuating frequency components of the PPG signal below a predetermined frequency band that includes the cardiac component and/or attenuates frequency components above the predetermined frequency band that includes the cardiac component, the predetermined frequency band spanning the full range of human heart rates.

7. The fitness monitor of claim 1, wherein the cardiac component is associated with heart rate, and wherein the determined time between successive cycles of the cardiac component is the time between successive heartbeats.

8. The fitness monitor of claim 1, wherein the processor is further configured to analyze the cardiac component of the PPG signal to determine heart-rate variability, stress, recovery time, VO2 max, and/or sleep quality of the user, based on the determined time between successive cycles of the cardiac component.

9. The fitness monitor of claim 1, further comprising a user interface coupled to the processor to display information based on the isolated cardiac component.

10. The fitness monitor of claim 1, further comprising a housing to enclose the processor, the housing including a means for attaching the fitness monitor to the user.

11. The fitness monitor of claim 1, wherein the determined filter coefficients include a center frequency corresponding to a fundamental frequency of the identified cardiac component of the PPG signal, and wherein the time-variant filter isolates the identified cardiac component by passing portions of the PPG signal associated with the center frequency.

12. The fitness monitor of claim 1, wherein the processor calculates the time between successive cycles of the isolated cardiac component by identifying similar peaks, troughs, or threshold-crossings of the isolated cardiac component in the successive cycles.

13. The fitness monitor of claim 1, wherein the processor identifies the cardiac component in the frequency domain by correlating one or more peaks of a motion signal with temporally consistent spectral peaks of the PPG signal.

14. A fitness monitor for monitoring a cardiac signal of a user, the device comprising:
    an emitter configured to transmit light toward skin of the user;
    a receiver configured to receive a reflection of the transmitted light and provide a photoplethysmogram (PPG)

signal based on the received reflection of the transmitted light, the PPG signal including a cardiac component and a motion component;

an inertial sensor configured to provide a motion signal based on sensed movement of the fitness monitor;

a time-variant filter configured to isolate a component of the PPG signal based on filter coefficients corresponding to undesired components of the PPG signal, and a processor coupled to the emitter, the receiver, the inertial sensor and the time-variant filter, the processor configured to:

determine one or more frequencies associated with the motion signal and the PPG signal provided during a first period, identify the motion component in the PPG signal for the first time period based on the determined one or more frequencies of the motion signal and the PPG signal, filter, via the time-variant filter, the identified motion component from the PPG signal provided during a second time period to isolate the cardiac component of the PPG signal for the second time period, and calculate, in the time domain, the time between successive cycles of the isolated cardiac component of the PPG signal for the second time period.

15. The fitness monitor of claim 14, wherein the first and second time periods correspond to the same period of time such that the filtered motion component is from the same instance of the PPG signal in which the motion component is identified.

16. The fitness monitor of claim 14, wherein the time-variant filter is integrated within the processor.

17. The fitness monitor of claim 14, wherein the processor is further configured to determine filter coefficients based on the identified motion component in the PPG signal for the first time period and configure the time-variant filter with the determined filter coefficients.

18. The fitness monitor of claim 14, wherein the cardiac component of the PPG signal for the second time period is isolated upon each occurrence of the motion component being identified based on the determined one or more frequencies of the motion signal and the motion component.

19. The fitness monitor of claim 14, further comprising a bandpass filter, wherein the processor is further configured to configure the bandpass filter to pre-condition the PPG signal by attenuating frequency components of the PPG signal below a predetermined frequency band that includes the cardiac component and/or attenuates frequency components above the predetermined frequency band that includes the cardiac component, the predetermined frequency band spanning the full range of human heart rates.

20. The fitness monitor of claim 14, wherein the cardiac component is associated with heart rate, and wherein the determined time between successive cycles of the cardiac component is the time between successive heartbeats.

21. The fitness monitor of claim 14, wherein the determined filter coefficients include a center frequency corresponding to a fundamental frequency of the identified motion component of the PPG signal for the first time period, and wherein the time-variant filter isolates the identified cardiac component during the second time period by not passing undesired components of the PPG signal associated with the center frequency.

22. The fitness monitor of claim 14, wherein the processor calculates the time between successive cycles of the isolated cardiac component by identifying similar peaks, troughs, or threshold-crossings of the isolated cardiac component in the successive cycles.

23. The fitness monitor of claim 14, wherein the processor identifies the motion component in the PPG signal for the first time period by correlating one or more peaks of a motion signal for the first time period with temporally consistent spectral peaks of the PPG signal.

24. A fitness monitor for monitoring a cardiac signal of a user, the device comprising:

an emitter configured to transmit light toward skin of the user;

a receiver configured to receive a reflection of the transmitted light and provide a photoplethysmogram (PPG) signal based on the received reflection of the transmitted light, the PPG signal including a cardiac component and a motion component;

an inertial sensor configured to provide a motion signal based on sensed movement of the fitness monitor;

a time-variant filter configured to isolate a component of the PPG signal based on filter coefficients corresponding to a desired component of the PPG signal, and a processor coupled to the emitter, the receiver, the inertial sensor and the time-variant filter, the processor configured to:

determine one or more frequencies associated with the motion signal and the PPG signal provided during a first time period, identify the cardiac component in the PPG signal for the first time period based on the determined one or more frequencies of the motion signal and the PPG signal, filter, via the time-variant filter, the PPG signal provided for a second time to isolate the cardiac component of the PPG signal for the second time period based on the identified cardiac component, and calculate, in the time domain, the time between successive cycles of the isolated cardiac component of the PPG signal for the second time period.

25. The fitness monitor of claim 24, wherein the time-variant filter is integrated within the processor.

26. The fitness monitor of claim 24, wherein the processor is further configured to determine filter coefficients based on the identified cardiac component in the PPG signal for the first time period and configure the time-variant filter with the determined filter coefficients.

27. The fitness monitor of claim 24, wherein the determined filter coefficients include a center frequency corresponding to a fundamental frequency of the identified cardiac component of the PPG signal, and wherein the time-variant filter isolates the identified cardiac component by passing portions of the PPG signal associated with the center frequency.

28. The fitness monitor of claim 24, wherein the processor calculates the time between successive cycles of the isolated cardiac component by identifying similar peaks, troughs, or threshold-crossings of the isolated cardiac component in the successive cycles.

29. The fitness monitor of claim 24, wherein the processor identifies the cardiac component in the PPG signal for the first time period by correlating one or more peaks of a motion signal for the first time period with temporally consistent spectral peaks of the PPG signal.

* * * * *